United States Patent
Svatos et al.

(10) Patent No.: US 10,417,390 B2
(45) Date of Patent: Sep. 17, 2019

(54) METHODS AND SYSTEMS FOR RADIOTHERAPY TREATMENT PLANNING

(71) Applicant: VARIAN MEDICAL SYSTEMS, INC., Palo Alto, CA (US)

(72) Inventors: Michelle Svatos, Oakland, CA (US); Corey Zankowski, San Jose, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 1035 days.

(21) Appl. No.: 14/754,742

(22) Filed: Jun. 30, 2015

(65) Prior Publication Data

US 2017/0004267 A1    Jan. 5, 2017

(51) Int. Cl.
  *G06F 19/00*    (2018.01)
  *A61N 5/10*    (2006.01)
  *G06N 7/00*    (2006.01)
  *G16H 50/20*    (2018.01)

(52) U.S. Cl.
  CPC .......... *G06F 19/3481* (2013.01); *A61N 5/10* (2013.01); *G06N 7/005* (2013.01); *G16H 50/20* (2018.01)

(58) Field of Classification Search
  CPC .... G06F 19/345; G06F 19/00; G06F 19/3481; G16H 50/20; G06N 7/0005
  USPC .......................................................... 703/5
  See application file for complete search history.

(56) References Cited

U.S. PATENT DOCUMENTS

| | | | | |
|---|---|---|---|---|
| 2002/0051513 A1* | 5/2002 | Pugachev | ............ | A61N 5/103 378/65 |
| 2010/0189220 A1* | 7/2010 | Flynn | .................... | A61N 5/103 378/65 |
| 2014/0032185 A1* | 1/2014 | Yepes | ................... | G16H 50/50 703/2 |
| 2015/0043878 A1 | 2/2015 | Chen | | |
| 2015/0199457 A1* | 7/2015 | Brand | ................ | G06F 17/5009 703/2 |

OTHER PUBLICATIONS

Geneviève Jarry and Frank Verhaegen 2007 Phys. Med. Biol. 52 2277. "Patient-specific dosimetry of conventional and intensity modulated therapy using a novel full monte carlo phase space reconstruction method from electronic portal images" ("Jarry") (Year: 2007).*

D Sawkey et al., "Evaluation of Motion Management Strategies Based on Required Margins", Physics in Medicine and Biology, 2012, pp. 6347-6369, No. 57.

(Continued)

*Primary Examiner* — Kamini S Shah
*Assistant Examiner* — Faraj Ayoub
(74) *Attorney, Agent, or Firm* — Su IP Consulting

(57) ABSTRACT

Example methods and systems for determining a treatment plan for a radiotherapy treatment system to deliver radiotherapy treatment to a patient are disclosed. In one embodiment, the method may comprise performing a particle transport simulation to initiate a first set of particle histories and a second set of particle histories from a radiation source of the radiotherapy treatment system to a treatment volume with multiple voxels representing an anatomy of the patient. The method may also comprise determining first cumulative costs associated with respective particle histories in the first set and second cumulative costs associated with respective particle histories in the second set. The method may further comprise selecting the first set or second set based on the first cumulative costs and second cumulative costs and determining the treatment plan based on the selected first set or second set.

17 Claims, 9 Drawing Sheets

(56) References Cited

OTHER PUBLICATIONS

Mischa Hoogeman et al., "Clinical Accuracy of the Respiratory Tumor Tracking System of the Cyberknife: Assessment by Analysis of Log Files", InT. J. Radiation Oncology Biol. Phys., 2009, pp. vol. 74, No. 1.

Geoffrey D Hugo et al., "Population and Patient-Specific Target Margins for 4D Adaptive Radiotherapy to Account for Intra-and Inter-Fraction Variation in Lung Tumor Position", Physics in Medicine and Biology, 2007, pp. 257-274, vol. 52.

Marcel Van Herk, Ph.D. et al., "The Probability of Correct Target Dosage: Dose-Population Histograms for Deriving Treatment Margins in Radiotherapy", InT. J. Radiation Oncology Biol. Phys., 2000, pp. 1121-1135, vol. 47, No. 4.

D Sawkey et al., "Evaluation of Motion Management Strategies Based on Required Margins", Physics in Medicine and Biology, 2012, pp. 6347-6369, vol. 57.

Cristian Cotrutz et al., "Using Voxel-Dependent Importance Factors for Interactive DVH-Based Dose Optimization", Physics in Medicine and Biology, 2002, pp. 1659-1669, vol. 47.

Yong Yang et al., "Inverse Treatment Planning with Adaptively Evolving Voxel-Dependent Penalty Scheme", Medicine Physics, Oct. 2004, pp. 2839-2844, vol. 31 No. 10.

Pavel Lougovski et al., "Toward Truly Optimal IMRT Dose Distribution: Inverse Planning with Voxel-Specific Penalty", Technol Cancer Res Treat., Dec. 2010, pp. 629-636, vol. 9, No. 6.

Stephen R Bowen et al., "On the Sensitivity of IMRT Dose Optimization to the Mathematical Form of a Biological Imaging-Based Prescription Function", Physics in Medicine and Biology, Mar. 21, 2009, pp. 1483-1501, vol. 54, No. 6.

Barbara Vanderstraeten et al., "[18F]Fluoro-Deoxy-Glucose Positron Emission Tomography ([18F]FDG-PET) Voxel Intensity-Based Intensity-Modulated Radiation Therapy (IMRT) for Head and Neck Cancer", Radiotherapy and Oncology, 2006, pp. 249-258, vol. 79.

Ludwig Bogner et al., "Fast Direct Monte Carlo Optimization Using the Inverse Kernel Approach", Physics in Medicine and Biology, 2009, pp. 4051-4067, vol. 54.

Thomas Dirscherl et al., "Feasibility of TCP-Based Dose Painting by Numbers Applied to a Prostate Case with 18F-Choline PET Imaging", Z. Med. Phys., 2012, pp. 48-57, vol. 22.

Luis A. Perez Romasanta et al., "Functional Imaging in Radiation Therapy Planning for Head and Neck Cancer", Reports of Practical Oncology and Radiotherapy, 2013, pp. 376-382, No. 18.

* cited by examiner

METHODS AND SYSTEMS FOR RADIOTHERAPY TREATMENT PLANNING

BACKGROUND

Unless otherwise indicated herein, the approaches described in this section are not prior art to the claims in this application and are not admitted to be prior art by inclusion in this section.

Radiotherapy is an important part of a treatment for reducing or eliminating unwanted tumors from patients. Unfortunately, applied radiation does not inherently discriminate between an unwanted tumor and any proximal healthy structures such as organs, etc. This necessitates careful administration to restrict the radiation to the tumor. Ideally, the goal is to deliver a lethal or curative radiation dose to the tumor (i.e., target), while maintaining an acceptable dose level in the proximal healthy structures. However, there are various challenges in devising a treatment plan that accurately delivers radiation doses as prescribed by a clinician.

SUMMARY

In accordance with some embodiments of the present disclosure, example methods and systems for determining a treatment plan for a radiotherapy treatment system to deliver radiotherapy treatment to a patient are provided.

In one embodiment, the method may comprise performing a particle transport simulation to initiate a first set of particle histories and a second set of particle histories from a radiation source of the radiotherapy treatment system to a treatment volume with multiple voxels representing an anatomy of the patient. The first set may be associated with a first radiation beam angle of the radiation source and the second set is associated with a second radiation beam angle of the radiation source. The method may also comprise determining first cumulative costs associated with respective particle histories in the first set and second cumulative costs associated with respective particle histories in the second set. Each of the first cumulative costs and second cumulative costs may be determined based on voxel-level costs associated with respective voxels on a path travelled by the associated particle history. The method may further comprise selecting the first set or second set based on the first cumulative costs and second cumulative costs; and determining the treatment plan based on the selected first set or second set.

In a second embodiment, the method may comprise performing a particle transport simulation to initiate a first set of particle histories and a second set of particle histories from a radiation source of the radiotherapy treatment system to a treatment volume with multiple voxels representing an anatomy of the patient. The first set may be associated with a first radiation beam angle of the radiation source and the second set is associated with a second radiation beam angle of the radiation source. The method may also comprise determining, for each particle history the first set and the second set, voxel-level costs associated with respective voxels on a path travelled by the particle history. Each voxel-level cost may be determined based on (i) a computed dose deposited by the particle history on the associated voxel and (ii) a spatially-varying desired dose of the associated voxel. The method may further comprise selecting the first set or second set based on the voxel-level costs; and determining the treatment plan based on the selected first set or second set.

DETAILED DESCRIPTION

Figure 1:
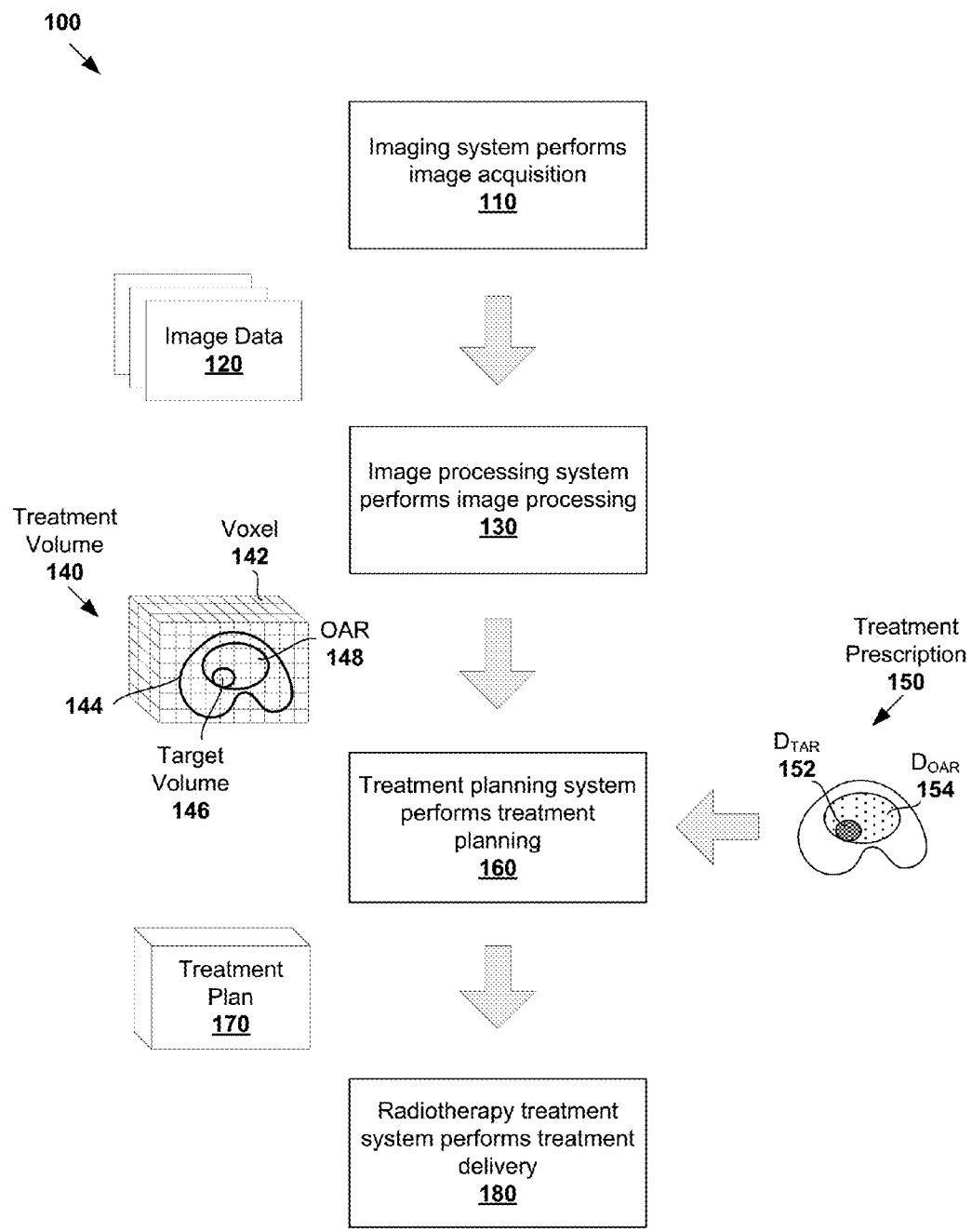
FIG. 1 is a schematic diagram of an example process of radiotherapy treatment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

FIG. 1 is a schematic diagram of example process flow 100 for radiotherapy treatment. Example process flow 100 may include one or more operations, functions, or actions illustrated by one or more blocks, such as 110 to 180. The various blocks may be combined into fewer blocks, divided into additional blocks, and/or eliminated based upon the desired implementation. In the example shown, radiotherapy treatment may generally include various stages, such as image data acquisition performed by an imaging system (see 110-120 in FIG. 1); image processing by an image processing system (see 130-140); treatment prescription by a clinician (see 150); treatment planning by a treatment planning system (see 160-170); and treatment delivery by a radiotherapy treatment system (see 180).

As will be further described below, treatment planning 160 may be improved according to the present disclosure to facilitate better treatment delivery. For example, given the often close proximity between tumors and proximal healthy structures (e.g., organs, etc.), any improvement in treatment planning has the potential of improving treatment outcome, such as increasing the tumor control probability and/or reducing the likelihood of minor through severe health complications or death due to radiation overdose in the proximal healthy structures.

Referring to FIG. 1, during image data acquisition 110, an imaging system may capture image data 120 of a patient's anatomy requiring radiotherapy treatment. Any suitable imaging modality or modalities may be used by the imaging system, such as computed tomography (CT), positron emission tomography (PET), magnetic resonance imaging (MRI), single photon emission computed tomography (SPECT), etc. When CT or MRI is used, image data 120 may include a series of two-dimensional (2D) images or slices, each representing a cross-sectional view of the patient's anatomy.

Next, during image processing 130 in FIG. 1, image data 120 may be processed by an image processing system, such as to reconstruct a three-dimensional (3D) volume of the patient's anatomy from image data 120. The 3D volume is known as "treatment volume" 140 that will be subjected to radiation. Treatment volume 140 may be divided into multiple smaller "voxels" 142 (i.e., volume-pixel), each representing a 3D element associated with location (i, j, k) within treatment volume 140. At this stage, information that is useful for subsequent treatment planning 160 may be extracted from treatment volume 140, such as the contour, shape, size and location of patient's anatomy 144, target volume 146 and any organ-at-risk (OAR) 148. In practice, target volume 146 may represent a malignant tumor (e.g., brain tumor) requiring radiotherapy treatment, and OAR 148 a proximal healthy structure (e.g., optic nerve, brain stem) that might be adversely affected by the treatment.

In practice, target volume 146 is also known as a planning target volume (PTV), and treatment volume 140 as an irradiated volume. Although a simple example is shown in FIG. 1, treatment volume 140 may include multiple target volumes 146 and OARs 148 with often complex shapes and sizes in practice. Each voxel (i, j, k) 142 may represent a density in treatment volume 140, such as according to a gray scale (e.g., solid, opaque, translucent, etc.). Although shown as having a regular shape (e.g., cube), voxel 142 may have any suitable shape (e.g., non-regular).

During treatment prescription 150 in FIG. 1, a clinician (e.g., oncologist, dosimetrist, etc.) may prescribe a radiotherapy treatment for the patient. For example, prescribed treatment 150 may include the desired radiation dose distributions for target volume 146 and OAR 148. This generally depends on the clinician's experience, the type and extent of the tumor, the patient's condition, etc. In general, a higher goal dose is prescribed for target volume 146 (denoted "$D_{TAR}$" at 152), and a lower goal dose for OAR 148 (denoted "$D_{OAR}$" at 154). Radiation dose may be measured in Gray, which represents the absorption of one joule of radiation energy in one kilogram of matter. A dose-volume histogram (DVH) may be used to summarize 3D dose distributions in a graphical two-dimensional (2D) format.

Next, during treatment planning 160 in FIG. 1, a treatment planning system may determine treatment plan 170 for a radiotherapy treatment system to perform treatment delivery (see 180) according to prescribed treatment 150 (e.g., dose distributions $D_{TAR}$ and $D_{OAR}$). As will be described further below using FIG. 2, treatment planning 160 generally takes into account the capabilities and limitations of the radiotherapy treatment system.

Treatment Plan

Figure 2:
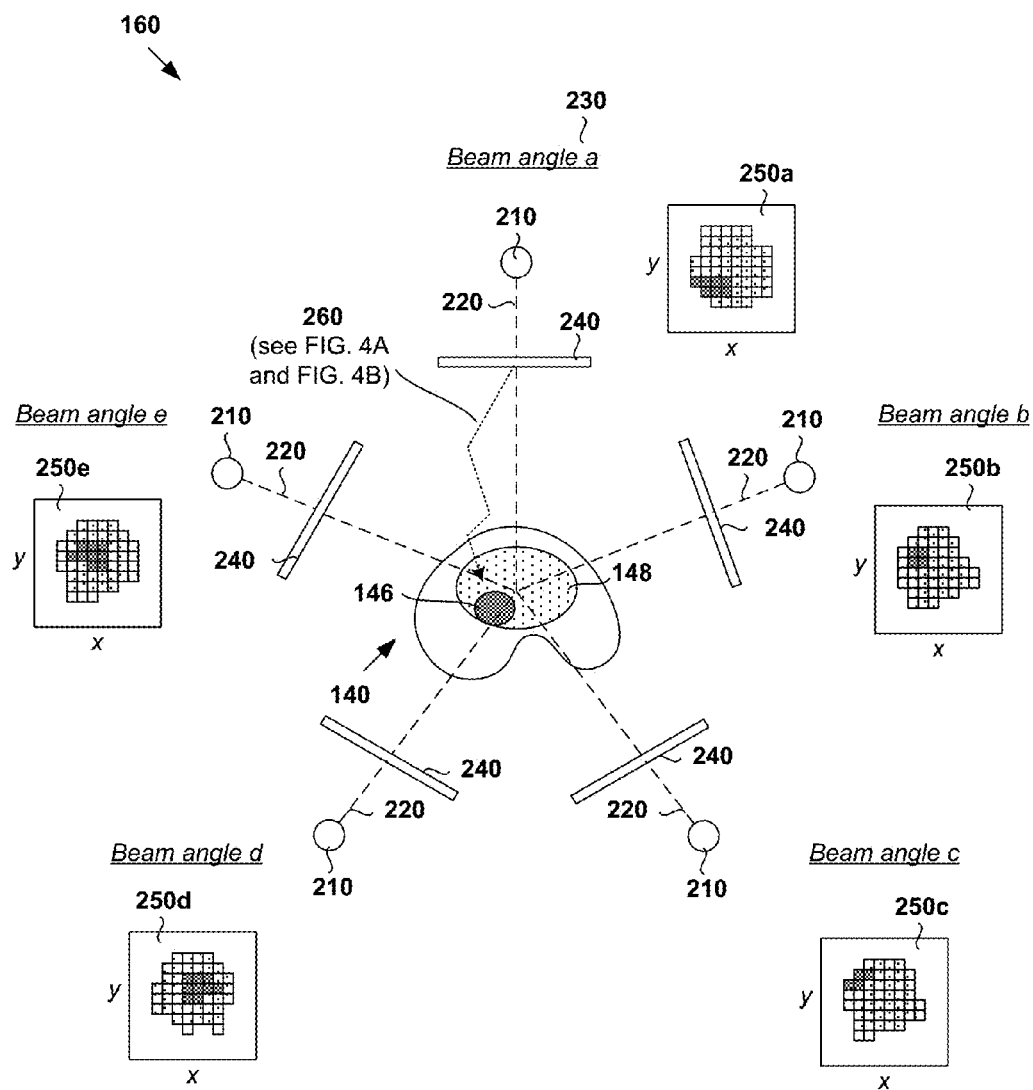
FIG. 2 is a schematic diagram of an example radiotherapy treatment planning to determine a treatment plan.

FIG. 2 is a schematic diagram of example radiotherapy treatment planning 160 to determine treatment plan 170. Radiotherapy treatment planning 160 may be performed to determine treatment plan 170 for a radiotherapy treatment system to deliver radiotherapy treatment to a patient. Although an example is shown in FIG. 2, it will be appreciated any alternative and/or additional configuration may be used depending on the desired implementation.

In the example in FIG. 2, the radiotherapy treatment system includes radiation source 210 to project radiation beam 220 onto treatment volume 140 representing the patient's anatomy at various beam angles 230. Although not shown in FIG. 2 for simplicity, radiation source 210 may include a linear accelerator to accelerate radiation beam 220 and a collimator (e.g., multileaf collimator (MLC)) to modify or modulate radiation beam 220. In another example, radiation beam 220 may be modulated by scanning it across a target patient in a specific pattern with various dwell times (e.g., as in proton therapy). A controller (e.g., computer system) may be used to control the operation of radiation source 220 according to treatment plan 170.

During treatment delivery 180, radiation source 210 may be rotatable (e.g., using a gantry) around a patient, or the patient may be rotated (as in some proton radiotherapy solutions) to emit radiation beam 220 at various beam angles 230 relative to the patient. For example, five equally-spaced beam angles 230 (e.g., angle α="a", "b", "c", "d" and "e"; also known as "fields") may be selected for radiation source 210. In practice, any suitable number of beam and/or table or chair angles 230 (e.g., five, seven, nine, etc.) may be selected. Increasing the number of angles 230 will generally increase the quality of the treatment. The treatment planning system, or any other suitable system, may be used to determine beam angles 230, such as using beam angle optimization, etc. At each beam angle 230, radiation beam 220 is associated with fluence plane 240 (also known as an intersection plane) situated outside the patient envelope along a beam axis extending from radiation source 210 to treatment volume 140. As shown, fluence plane 240 is generally at a known distance from the isocenter.

In addition to beam angles 230, fluence parameters of each radiation beam 220 are required for treatment delivery 180 using a radiotherapy treatment system. The term "fluence parameters" may refer generally to characteristics of radiation beam 220, such as its intensity profile as represented using 2D "fluence maps" (e.g., 250a, 250b, 250c, 250d and 250e for corresponding beam angles 230 "a", "b", "c", "d" and "e"). In the following, fluence maps 250a, 250b, 250c, 250d and 250e may also be referred to collectively as "fluence maps 250" or individually as "fluence map 250". Each fluence map (e.g., 250a) represents the intensity of radiation beam 220 at each point (x, y) on fluence plane 240 at a particular beam angle 230 (e.g., "a"). Treatment delivery 180 may then be performed according to fluence maps 250, such as using intensity modulation radiation therapy (IMRT), etc.

The process of determining fluence maps 250 (often called fluence map optimization) may be performed during treatment planning 160 in FIG. 1. In particular, each fluence map 250 may be determined by varying the intensity or weight of radiation at each point (x, y) in order to satisfy a clinician's prescribed treatment 150. The amount of radiation dose deposited on treatment volume 140 by radiation beam 220 from a particular point (x, y) may be calculated using any suitable, such as particle transport simulation using Monte Carlo techniques, convolution, Fourier transformation, superposition, directly solving the Boltzmann equations, or any other dose calculation approach, etc. For example, particle transport simulation may be performed to initiate a "particle history" (see 260 in FIG. 2) of radiation beam 220 along a path from radiation source 210 to treatment volume 140.

Throughout the present disclosure, the term "particle" may refer generally to a discrete packet of energy, such as photons, protons, electrons, ions, or any other particles from electromagnetic radiation (e.g., gamma-rays, x-rays, etc.), etc. Along the path between radiation source 210 and treatment volume 140, an interaction may occur between the particle and a matter through which it is passing (e.g., air, water, bone, tissue, etc.). For example, photon interactions may include incoherent (Compton) scattering; pair production; photo-electric absorption; and coherent (Rayleigh) scattering, etc. The term "particle history" may refer generally to the complete path of a primary particle (e.g., photon) and any secondary particle (e.g., electron) generated due to one or more interactions, and all its associated energy deposition into the volume of interest.

The radiation dose deposited according to fluence maps 250 should, as much as possible, correspond to prescribed treatment 150 (see FIG. 1). However, fluence maps 250 that are optimal are quite difficult to determine due to the conflicting goals of delivering a prescribed radiation dose (e.g., $D_{TAR}$) to target volume 146 while maintaining an acceptable radiation dose (e.g., $D_{OAR}$) on OAR 148. Further, both target volume 146 and OAR 148 often have complex 3D shapes, thereby compounding the difficulty of treatment planning 160.

Treatment Planning

According to examples of the present disclosure, treatment planning 160 may be improved to converge faster (e.g., to an optimal solution) and with more fidelity to clinical objectives, especially when there are many constraints involved. In the following, (a) a first embodiment of the present disclosure will be explained using FIG. 3 and FIG. 4A, and (b) a second embodiment using FIG. 4B and FIG. 5. Examples of the first embodiment and/or second embodiment may shine in situations where there is a high complexity, such as when a constraint is defined for each voxel 142 (or group of voxels 142) in patient's image data 120. Improved accuracy may greatly increase the chance of curing target volume 146, and/or decrease the chance of damaging normal tissue in OAR 148 that may lead to undesirable side effects.

It should be understood that the first and second embodiments may be implemented independently in different treatment planning systems. Alternatively, as will be discussed using FIG. 6, FIG. 7 and FIG. 8, the first and second embodiments may also be used together during treatment planning 160.

(a) Cumulative Cost for Particle History

According to a first embodiment, treatment planning 160 may be improved by determining a "cumulative cost" (see 320 in FIGS. 3 and 440 in FIG. 4A) associated with each particle history initiated during simulation. The cumulative cost associated with a particular particle history may be determined based on voxel-level costs of respective voxels on a path of that particular particle history. Particle histories that are most beneficial for treatment plan 170 may then be selected based on their respective cumulative costs.

Figure 3:
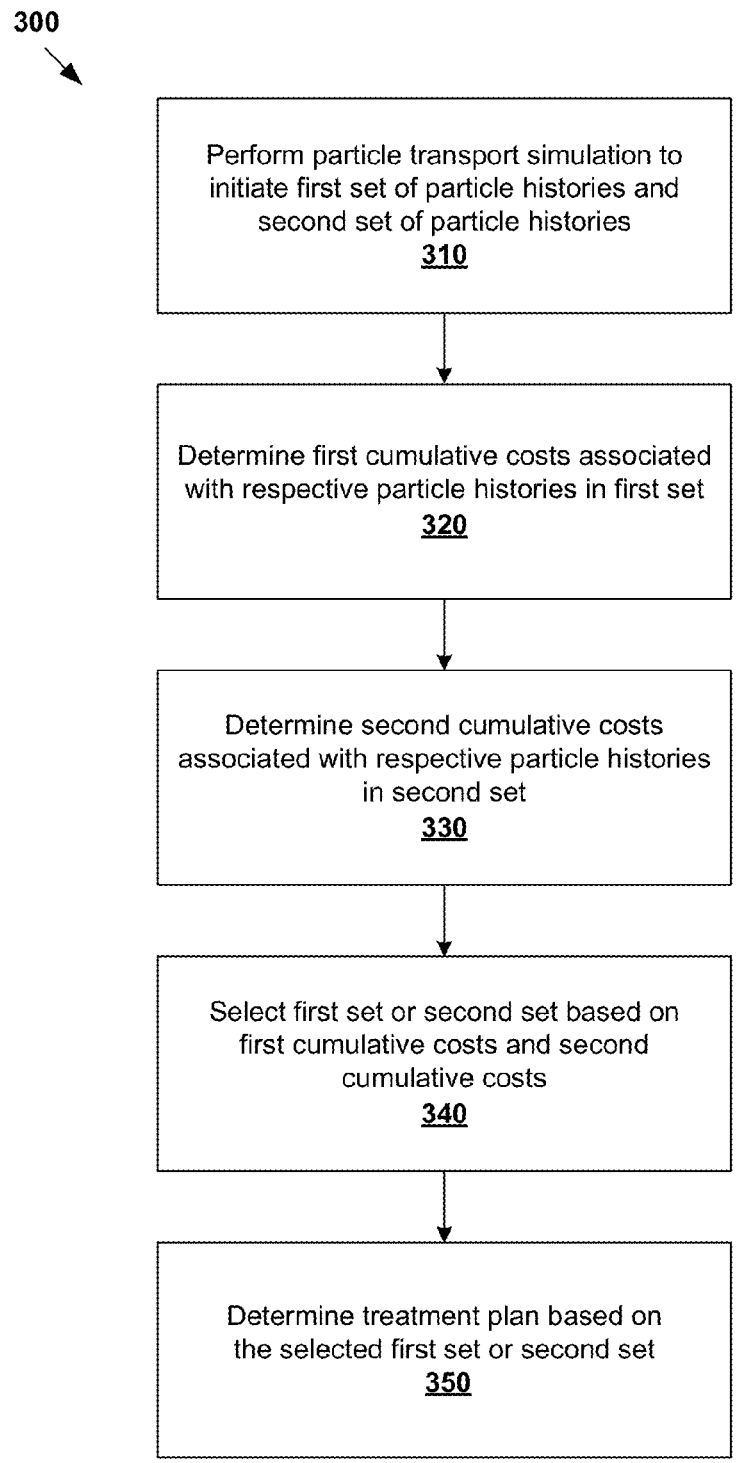
FIG. 3 is a flow diagram of an example process to determine a radiotherapy treatment plan for a radiotherapy treatment system according to a first embodiment of the present disclosure.

In more detail, FIG. 3 is a flow diagram of example process 300 to determine radiotherapy treatment plan 170 for radiotherapy treatment system 180 according to a first embodiment of the present disclosure. Example process 300 may include one or more operations, functions, or actions illustrated by one or more blocks, such as 310 to 350. The various blocks may be combined, divided, and/or eliminated based upon the desired implementation. Blocks 310 to 350 in FIG. 3 may be performed by any suitable treatment planning system. FIG. 3 will be discussed with reference to FIG. 4A, which is a schematic diagram of example radiotherapy treatment planning 160 according to the first embodiment in FIG. 3.

Figure 4A:
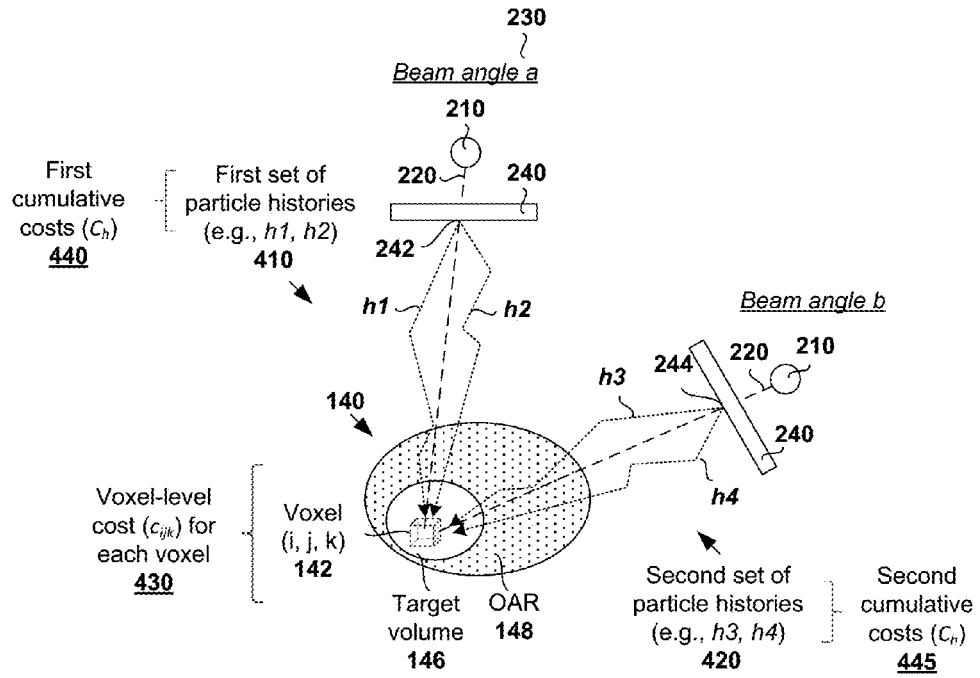
FIG. 4A is a schematic diagram of an example radiotherapy treatment planning according to the first embodiment in FIG. 3.

At block 310 in FIG. 3, a particle transport simulation is performed to initiate multiple sets of particle histories (e.g., 410 and 420 in FIG. 4A) from radiation source 210 to treatment volume 140 with multiple voxels 142 (one shown for simplicity in FIG. 4A) that represent a patient's anatomy. Any suitable number of sets may be used but for simplicity, two sets are shown in FIG. 4A. First set 410 is associated with first angle 230 (e.g., "a") and initiated via first fluence point 242 on fluence plane 240. Second set 420 is associated with second angle 230 (e.g., "b") and initiated via second fluence point 244 on fluence plane 240.

Any suitable simulation technique may be used, such as Monte Carlo simulation that determines the path of each particle history in first set 410 and second set 420 using a random number generator and probability distribution functions relating to possible interactions, etc. In the example in FIG. 4A, first set 410 includes two particle histories (e.g., h1 and h2) that travel from fluence plane 240 of radiation beam 220 at angle="a" to treatment volume 140. Second set 420 includes two particle histories (e.g., h3 and h4) that travel from fluence plane 240 of radiation beam 220 at angle="b" to treatment volume 140. Although two particle histories are shown in each set 410/420, any number (e.g., hundreds to millions) of particle histories may be initiated in practice.

At blocks 320 and 330 in FIG. 3, first cumulative costs 440 associated with respective particle histories in first set 410 and second cumulative costs 445 associated with second set 420 are determined. Each cumulative cost associated with a particular particle history h may be denoted as "$C_h$". For example in first set 410 in FIG. 4A, first cumulative costs 440 $C_{h1}$ and $C_{h2}$ may be determined for respective particle histories h1 and h2. Similarly, for second set 420 in FIG. 4A, cumulative costs 445 $C_{h3}$ and $C_{h4}$ may be determined for respective particle histories h3 and h4.

As will be discussed further using FIG. 6, the term "cumulative cost" ($C_h$) associated with a particle history may refer generally to the positive effect (i.e., benefit) or negative effect (i.e., penalty) of the particle history to assist the selection process at 340 in FIG. 3. As used herein, if the cost is positive, the effect is a net negative (e.g., dose in OAR 148); whereas if the cost is negative, the effect is a net benefit (e.g., dose in target volume 146). Alternatively, the reverse may be used, i.e., positive cost to represent a net benefit (e.g., dose in target volume 146), and negative cost to represent a net negative effect (e.g., dose in OAR 148). In both cases, the cumulative cost is used to improve (e.g., maximize) the net benefit and/or reduce (e.g., minimize) the net negative effect.

The cumulative cost associated with a particle history (e.g., $C_{h2}$ for h2) may be determined based on voxel-level costs associated with respective voxels (one shown at 142 in FIG. 4A for simplicity) on the path travelled by the particle history (e.g., h2). For simplicity, one voxel 142 is shown in FIG. 4A on the path travelled by a particle history (e.g., h2). Using voxel 142 as an example, the voxel-level cost ($c_{ijk}$) may be determined based on (i) a computed dose ($d_{ijk}$) deposited by the particle history (e.g., h2) on voxel 142 and (ii) a desired dose ($D_{ijk}$) for voxel 142. The desired dose ($D_{ijk}$) may be a mean prescribed dose to an organ or structure (e.g., DTAR at 152 and DOAR at 154 in FIG. 1), or a spatially-varying desired dose according to the second embodiment below.

Similarly, the term "voxel-level cost" ($c_{ijk}$) associated with a voxel on a path travelled by an associated particle history may refer generally to a positive effect (i.e., benefit) or negative effect (i.e., penalty) of the voxel. As used herein, if the cost is positive, the effect is a net negative (e.g., dose in a voxel within OAR 148); whereas if the cost is negative, the effect is a net benefit (e.g., dose in a voxel within target volume 146). Alternatively, the reverse may be used, i.e., positive cost to represent a net benefit (e.g., dose in a voxel within target volume 146), and negative cost to represent a net negative effect (e.g., dose in a voxel within OAR 148). In both cases, the voxel-level costs may be used to improve (e.g., maximize) the net benefit and/or reduce (e.g., minimize) the net negative effect.

At block 340 in FIG. 3, first set 410 (e.g., h1 and h2) or second set 420 (e.g., h3 and h4) may be selected for treatment plan 170 based on first cumulative costs 440 (e.g., $C_{h1}$ and $C_{h2}$) and second cumulative costs 445 (e.g., $C_{h3}$ and $C_{h4}$). For example, first set 410 and second set 420 may be ranked and saved by comparing first cumulative costs 440 (e.g., sum of $C_{h1}$ and $C_{h2}$) with second cumulative costs 445 (e.g., sum of $C_{h3}$ and $C_{h4}$) to select the most favorable or "winning" particle histories (e.g., h1 and h2 if first set 410 is selected).

At block 350 in FIG. 3, treatment plan 170 may be determined based on selected first set 410 or second set 420. In practice, treatment plan 170 may be determined based on fluence parameters associated with the particle histories of the selected first set 410 or second set 420. As discussed using FIG. 2, the fluence parameters may represent intensity profiles of radiation beam 220 of radiation source 210 at angle="a" associated with first set 410 or angle="b" associated with second set 420.

The use of cumulative costs according to examples of the present disclosure should be contrasted with the conventional approach of averaging the cost over the whole treatment volume 140 (e.g., organ). Such conventional approach results in unfavorable hot or cold spots, even though the average or mean dose is acceptable. In practice, this is a problematic because a physician always has to review the results slice by slice to determine if the resulting treatment plan is acceptable, even if the organ goals are met. This necessitates multiple meetings with the physicist or dosimetrist during treatment planning. The planner has to then go back and "fiddle" with the calculation or optimization (e.g., by adjusting goals and constraints, etc.) in order to try to get a better treatment plan. Further, the individual particle information is not stored, so they have to either start over, or continue the optimization process on top of the previous optimization.

However, by determining voxel-level costs and cumulative costs according to example process 300, practitioners are able to keep track of the "good" (low cost) particles and therefore more likely to determine a more effective treatment plan sooner. In example process 300, particle histories in first set 410 and second set 420 may be ranked to give priority to those that worked the best, throwing out the ones that did not add good value (benefit). All the information on the best or optimal particle histories may be stored and the ideal fluence map may be determined out of these particle histories.

(b) Voxel-Level Cost Based on Spatial Information

As discussed using blocks 320 and 330 in FIG. 3, a voxel-level cost ($c_{ijk}$) for voxel 142 may be determined based on a mean desired dose (e.g., $D_{TAR}$ 152 and $D_{OAR}$ 154 in FIG. 1). In particular, the voxel-level cost may be determined using the following cost functions ($n \geq 1$):

PTV dose cost function: $c_{ijk} = (d_{ijk} - D_{TAR})^{2n}$

OAR dose cost function: $c_{ijk} = (d_{ijk} - D_{OAR})^{2n+1}$

The above approaches are designed to look at the macro properties of target volume 146 or OAR 148, which means all voxels within target volume 146 or all voxels within OAR 148 are essentially treated as interchangeable equals. In particular, they assume that all voxels 142 within target volume 146 will have the same desired dose of $D_{TAR}$ 152, and voxels 142 within OAR 148 will the same desired dose of $D_{OAR}$ 154. While the macro properties may map well to clinical understanding, they generally do not provide fine control over the radiation dose delivered to a particular voxel 142. As such, even when the dose-volume constraints (e.g., $D_{TAR}$ 152 and $D_{OAR}$ 154) are met, the resulting treatment plan 170 might not be considered suitable for implementation once the isodose lines of the overall dose distribution are studied.

According to a second embodiment of the present disclosure, the voxel-level cost ($c_{ijk}$) is determined not only based on the above macro properties, but also the geometry of a patient's anatomy. Instead of assuming one general constraint (e.g., $D_{TAR}$ 152 or $D_{OAR}$ 154) per anatomical structure, various voxel-level constraints relating to "spatial information" (see 450 and 460 in FIG. 4B, and 520 in FIG. 5) of that voxel 142 may be considered during treatment planning 160, such as structure type, proximity to target volume 146, etc. For simplicity, second set 420 is not shown in FIG. 4B, but it will be appreciated that the following also applies to particle histories in second set 420, or any additional or alternative set(s).

The second embodiment of the present disclosure may take advantage of different types of information to drive treatment planning 160, such as detailed imaging information (e.g., continuously varying functional image signals that dictate hot and cold pockets of desired dose) from image data 120, or desired dose fall-off of a certain gradient from target volume 146 to protect OAR 148. This in turn facilitates radiotherapy that is closer to an ideal of highly sculpted dose deliveries, also referred to as "dose painting".

Figure 4B:
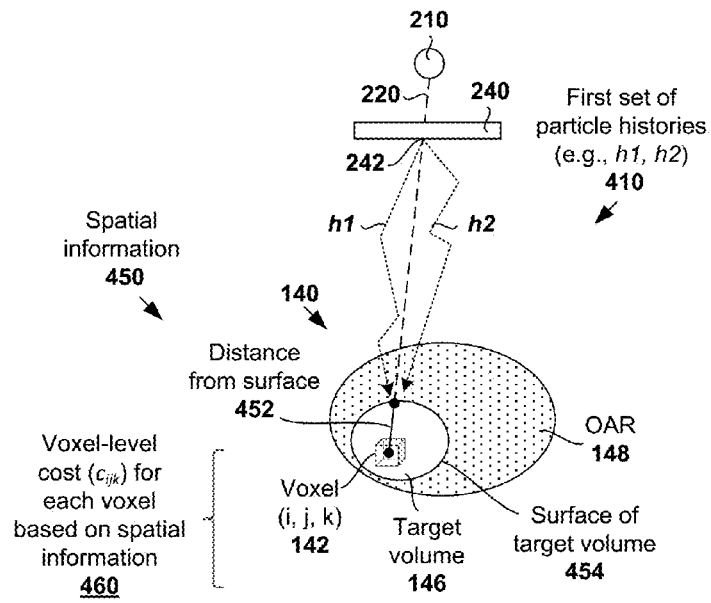
FIG. 4B is a schematic diagram of an example radiotherapy treatment planning according a second embodiment in FIG. 5.
Figure 5:
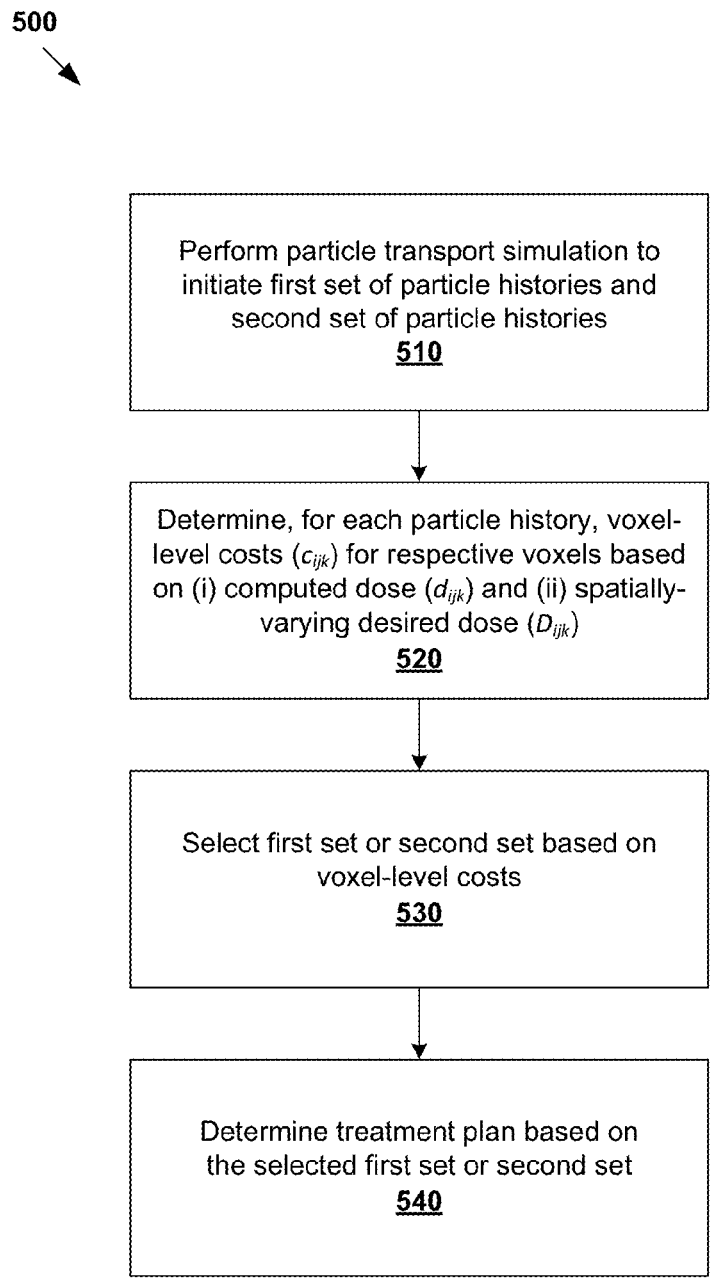
FIG. 5 is a flow diagram of an example process to determine a radiotherapy treatment plan for a radiotherapy treatment system according to a second embodiment of the present disclosure.

In more detail, FIG. 5 is a flow diagram of example process 500 to determine radiotherapy treatment plan 170 for radiotherapy treatment system 180 according to a second embodiment of the present disclosure. Example process 500 may include one or more operations, functions, or actions illustrated by one or more blocks, such as 510 to 540. The various blocks may be combined, divided, and/or eliminated based upon the desired implementation. Blocks 510 to 540 in FIG. 5 may be performed by a treatment planning system (see 160 in FIG. 1). FIG. 5 will be discussed with reference to FIG. 4B, which is a schematic diagram of example treatment planning 160 according to the second embodiment in FIG. 5.

At block 510 in FIG. 5 (similar to 310 in FIG. 3), a particle transport simulation is performed to transport multiple sets of particle histories (e.g., first set 410 in FIG. 4B and second set 420 explained using FIG. 1A) from radiation source 210 (e.g. via respective first fluence point 242 and second fluence point 244 in FIG. 4B) to treatment volume 140 with multiple voxels 142 (one shown for simplicity) representing a patient's anatomy. As discussed, any suitable simulation techniques may be used, such as Monte Carlo particle transport, etc.

At block 520 in FIG. 5, for each particle history (e.g., h2) is transported, voxel-level costs (each denoted $c_{ijk}$, see 460 in FIG. 4B) associated with respective voxels 142 (one shown for simplicity) on a path travelled by the particle history (e.g., h2) are determined. Using voxel 142 as an example, the voxel-level cost ($c_{ijk}$) may be determined based on (i) a computed dose ($d_{ijk}$) deposited by that particle history (e.g., h2) on voxel 412 and (ii) a desired dose ($D_{ijk}$) for voxel 412 that is associated with spatial information of the voxel within the treatment volume (see 450 in FIG. 4B).

For example in FIG. 4B, the spatial information 450 may include distance 452 of voxel 142 relative to surface 454 of target volume 146. A spatially varying probability of voxel 142 being within target volume 146 (e.g., tumor) or within OAR 148 may also be used to drive a spatial dose distribution. A probability density function can describe uncertainty in tumor position (e.g., caused by motion), which could be used to modulate a penalty associated with voxel 142. If voxel 142 has 80% chance of being tumor, its associated voxel-level cost may be set to $0.8 \times c_{ijk}$. A functional image (e.g., PET) creates a continuous signal and not a sharp binary distinction between tumor and normal tissue. This continuous function can also be represented by a probability density function that is spatially dependent, in which case it would also result in spatial modulation of voxel-level cost 460.

The spatial information may also come from imaging studies that highlight a function of a region in which voxel 142 is located. In this case, highly functioning regions may be avoided, and thus spared (by putting a high cost on those voxels 142. For example, functional magnetic resonance imaging (fMRI) studies of the brain show which regions of the brain are used for specific tasks. If the patient is a professional flute player, it might make sense to avoid the portion of her brain that is used when playing the flute. Also, in the lung, it is possible to image which regions of the lung is actively ventilating, and which regions are diseased and dead. In this case, it would be preferable to put the radiation beams 230 through regions of the lung that are already "dead" in order to avoid further damage. For example, assigning a low cost to voxels in these regions would accomplish that.

At block 530 in FIG. 5, first set 410 (e.g., h1 and h2) or second set 420 (e.g., h3 and h4) may be selected for treatment plan 170 based on the voxel-level costs ($c_{ijk}$) 460 determined at block 520. Similar to the examples in FIG. 3 and FIG. 4A, the selected particle histories (e.g., h1 and h2 if first set 410 is selected or h3 and h4 if second set 420 is selected) may be referred to as "winning" histories.

At block 540 in FIG. 5 (similar to 350 in FIG. 3), treatment plan 170 may be determined based on the particle histories of selected first set 410 (e.g., h1 and h2) or second set 420 (e.g., h3 and h4). In practice, treatment plan 170 may be determined based on fluence parameters associated with the particle histories of the selected first set 410 or second set 420. As discussed using FIG. 2, the fluence parameters (e.g., fluence maps 250) may represent intensity profiles of radiation beam 220 of radiation source 210.

In the following, an example of treatment planning 160 that takes advantage of both the first embodiment and second embodiment will be discussed using FIG. 6, FIG. 7A, FIG. 7B and FIG. 8. As mentioned above, the embodiments may also be used independently in different systems. FIG. 6 is a flow diagram of example process 600 to determine radiotherapy treatment plan 170 for radiotherapy treatment system 180 according to the first embodiment and the second embodiment of the present disclosure. Example process 600 may include one or more operations, functions, or actions illustrated by one or more blocks, such as 605 to 690. The various blocks may be combined, divided, and/or eliminated based upon the desired implementation. Example process 600 may be performed by treatment planning system 160 (see also FIG. 9).

Pre-Processing

Figure 6:
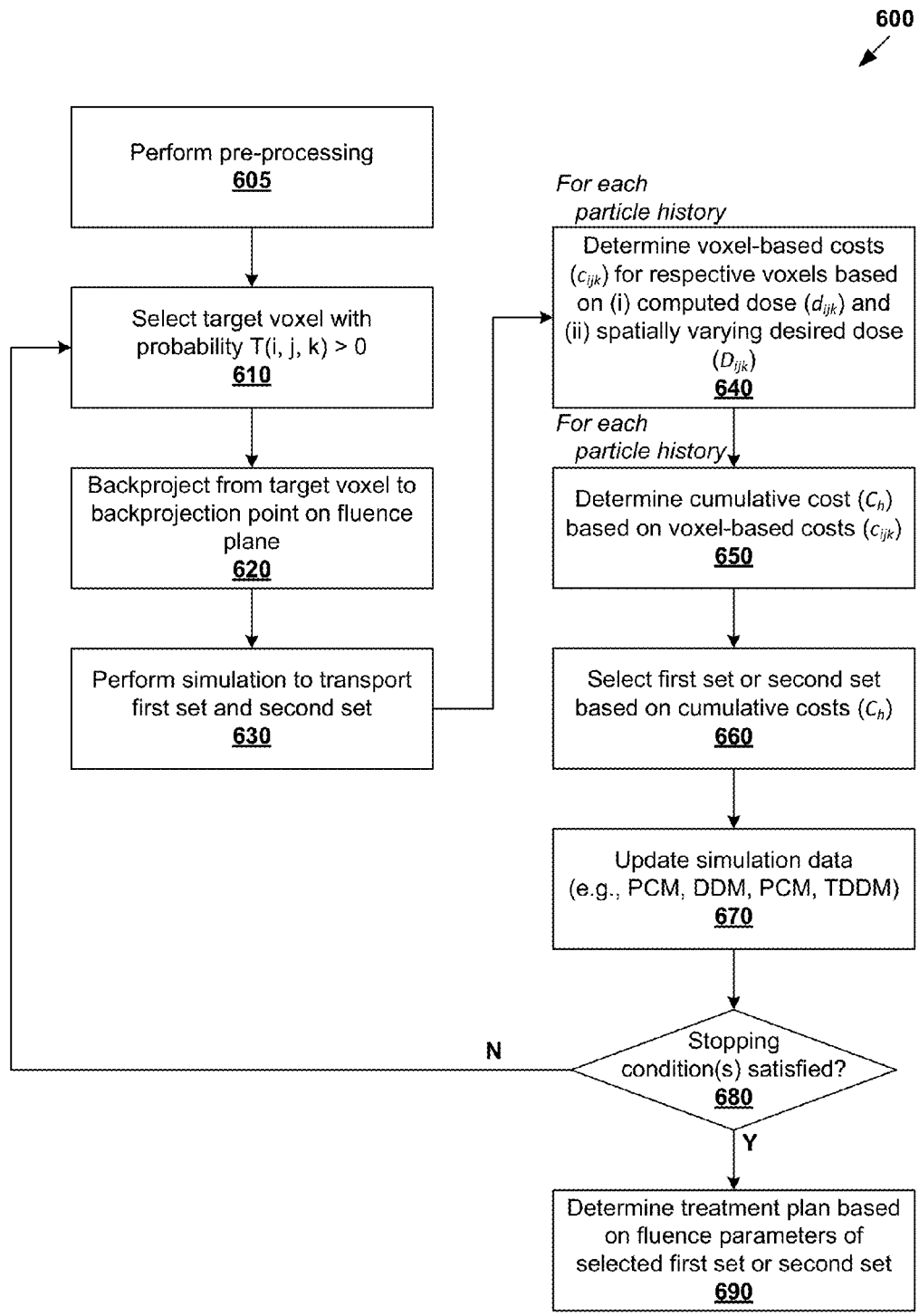
FIG. 6 is a flow diagram of example process to determine a radiotherapy treatment plan for a radiotherapy treatment system according to the first embodiment and the second embodiment of the present disclosure.

At block 605 in FIG. 6, a pre-processing step may be performed, such as to prepare the geometry for subsequent particle transport. In particular, one or more of the following simulation data may be initialized or established.

(i) Patient Target Matrix (PTM)

A PTM may be established to include matrix elements T(i, j, k) that each represent the probability of a tumor being found at voxel (i, j, k). Any suitable form of probability distribution function (PDF) may be used for T(i, j, k), such as a discrete or continuous function. In one example, T(i, j, k) may be a binary function where a voxel (i, j, k) is either "in" or "out" of target volume 146. If "in", T(i, j, k)=0 represents voxel (i, j, k) having 0% chance of being part of target volume 146. Otherwise, if "out", T(i, j, k)=1 represents voxel (i, j, k) having 100% chance of being part of target volume 146. Since T(i, j, k) is a voxel-based function, it may also be formulated to represent multiple target volumes 146 that are spatially distributed within treatment volume 140 (i.e., voxel in any target volume 146 having T(i, j, k)>0).

In another example, T(i, j, k) may be a continuous function representing the statistical probability voxel being part of target volume 146. Unlike a binary function, the continuous function allows for intermediate values derived from multiple sources of uncertainties, such as motion blurring, positioning, measurement, imaging error, etc. For example, the continuous function may be based on confidence levels from imaging studies such as Standardized Uptake Values (SUVs) from PET images or blurring due to motion distributions. In this motion case, T(i, j, k) may account for an uncertainty associated with target volume 146 due to a motion of the patient when image data 120 is captured during image acquisition 110, such as a breathing motion, a cardiac motion, or an irregular motion, etc.

In practice, there may be uncertainty in the voxel assignment (e.g., whether a voxel is a tumor or an organ, which organ the voxel belongs to, etc.) due to spatial proximity, motion, low quality image that makes it hard to distinguish between tissues, etc. Such uncertainty may be accounted for using any suitable approach. Using an analytic approach, if the voxel has 80% chance of being tumor and 20% chance of being OAR tissue, a weighted-sum cost is calculated by weighting the target cost, weighting the OAR cost by 0.2 before adding them together. Using a probabilistic approach (e.g., statistical interpolation), a random number between 0 and 1 may be generated. If the number is equal or less than 0.8, the voxel would be called a tumor. Otherwise, the voxel would be called an OAR. In another example, if a voxel consists of 70% prostate tissue and 30% rectal tissue, the voxel would be called tissue prostate if the random number is less than or equal to 0.7, or rectal tissue otherwise. After repeating this for a large number of particle histories (e.g., millions), the answers would be a correct mixture of both.

The PDF may be converted into a normalized cumulative probability density function (NCPDF) that is indexed by a random number between 0 and 1 to select a corresponding random voxel (i, j, k) within the PDF. A simple one-dimensional binary function looks like a square function, with its corresponding NCPDF may have a straight line starting from zero at the left target border and reaching one at the right border. During subsequent particle transport simulation, Monte Carlo methods may be used to locate a random voxel (i, j, k) within target volume 146 based on the NCPDF.

(ii) Proximity Matrix (P) and Dose Matrix ($\hat{d}_{min}$)

Proximity matrix (P) and expected achievable dose matrix ($\hat{d}_{min}$) may be established to capture voxel's 142 spatial information (see 450 in FIG. 4B) according to examples of the second embodiment. For example, each matrix element P(i, j, k) may represent the closest distance of voxel (i, j, k) to an edge or surface of target volume 146 (see 452 and 454 in FIG. 4B). Proximity matrix P may be established for each direction radiation beam 220, such as $P_a$ for angle="a", $P_b$ for "b", and so on, for the example in FIG. 2B. To reduce computational efforts, proximity matrix P may be computed for a number of directions, and then interpolated when required to get a reasonable value for other directions.

Achievable dose matrix ($\hat{d}_{min}$) includes matrix elements $\hat{d}_{min}$(i, j, k) that each represent the minimum or expected dose achievable at voxel (i, j, k) based on P(i, j, k). For voxels 142 within OAR 148, $\hat{d}_{min}$(i, j, k) may represent the minimal dose that can be expected given prescribed dose $D_{OAR}$ 154, voxel location from surface 454 of target volume 146, and the anatomical/geometric specifics of the patient. This is generally lower than the tolerance of the structure within which voxel 142 is located. For voxels 142 within target volume 146, $\hat{d}_{min}$(i, j, k) may be based on prescribed dose $D_{TAR}$, which is often specified as a minimum dose to the target. In most cases, the center of a PDF has the highest probability of finding tumor. In such a case, a higher dose may be applied to the center, which means more dose will go to where there is a higher probability of finding tumor cells. Later on, modulation may be performed to create a higher dose in the middle of target volume 146 (e.g., generally preferred in radiosurgery).

Figure 7A:
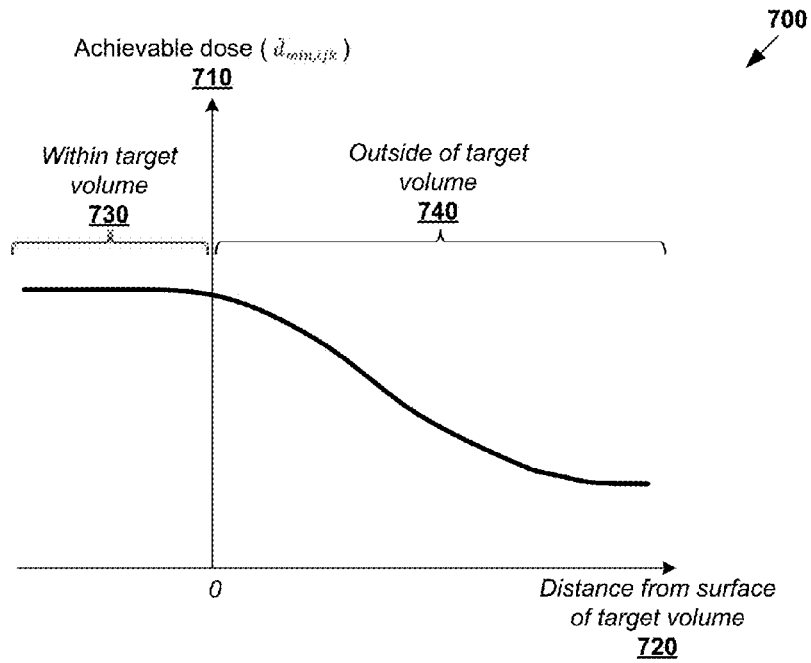
FIG. 7A is a simplified graph of achievable dose at a voxel plotted as a function of its distance from the surface of a target volume.

To better illustrate an example of the spatially varying cost function, FIG. 7A is a simplified graph of achievable dose $\hat{d}_{min}$(i, j, k) at voxel (i, j, k) plotted as a function of its distance from surface 454 of target volume 146. See corresponding y-axis 710 and x-axis 720. In this example, negative distance (see 730) indicates that the voxel (i, j, k) is within target volume 146, and positive distance (see 740) outside of target volume 146. Achievable dose $\hat{d}_{min}$(i, j, k) decreases as the distance increases from negative to zero (i.e., representing surface 454 of target volume 146) and then to the positive region (i.e., increasingly further away from target volume 146).

The above takes advantage of insights stemming from the population analysis of hundreds of dose distributions resulting from intensity modulation radiotherapy (IMRT), which suggests that patient anatomy proximity is the principle component driving the shape of the achievable dose. Statistically, the dose achievable at a particular target voxel (i, j, k) within a patient is a function of its distance from the boundary of the surface of target volume 146. Intuitively, the further away a voxel is from target volume 146, the lower the expected dose to the voxel. Note that the "surface" 454 may be more arbitrary if a PDF is used to describe its extent (e.g., full width at half maximum (FWHM)).

(iii) Patent Dose Matrix (PDM)

A PDM may be established to store the amount of dose deposited. In particular, each matrix element PDM(i, j, k) may represent the amount of dose deposited for each voxel (i, j, k). At the start of the simulation, PDM is initialized to all zeros. After each round of particle transport, PDM is updated incrementally with the simulated dose ($d_{ijk}$) deposited by a selected particle history.

(iv) Target Dose Deficit Matrix (TDDM)

A TDDM may be established to include matrix elements TDDM(i, j, k) that each represent the dose deficit at voxel (i, j, k). The dose deficit is the prescribed or desired dose ($D_{ijk}$) minus the total dose delivered (e.g., stored in PDM(i, j, k)) so far. The TDDM may be used as a driver to the subsequent particle transport simulation and updated after each round of particle transport. For example, one stopping condition for the particle transport simulation may be TDDM(i, j, k)=0 for all voxels (i, j, k).

(v) Patient Cost Matrix (PCM)

A PCM may be established to store the voxel-level cost ($c_{ijk}$) discussed at 430 in FIG. 4A and 460 in FIG. 4B. Each matrix element PCM(i, j, k) may represent the "cost" ($c_{ijk}$) of depositing a certain amount of simulated dose ($d_{ijk}$) onto voxel (i, j, k). In one example, subsequent selection of particle histories may be based on a cost minimization process. For a voxel (i, j, k) within target volume 146, the cost is negative (i.e., a benefit), but otherwise the cost is positive (i.e., a penalty to discourage dose deposition, especially on OAR 148). It will be appreciated that the reverse may be used, in which case a cost maximization process may be used in alternative implementations. More generally, in each case, cost minimization or cost maximization is performed for benefit maximization.

Particle Transport Simulation

Once pre-processing is performed, particle transport simulation may be performed according to block 310 in FIG. 3 and block 510 in FIG. 5. In the following examples, Monte Carlo will be used for particle transport but it will be appreciated that other techniques may be used. Monte Carlo particle transport simulation when correctly implemented is very accurate physically. The following examples should be contrasted with existing approaches that use many iterations of a faster (but less accurate) transport and recalculate a final (or immediate) answer with a more accurate code at the end, allowing for a mismatch between the ideal and final fluence parameters.

To start the simulation, desired beam angles for radiation beam 220 are first determined, such as angle="a" for first set 410 and angle="b" for second set 420 discussed using FIG. 2 and FIG. 4A. Any additional or alternative beam angles may be used to initiate additional or alternative sets. For example, at particular angle 230 (e.g., "a"), radiation beam 220 may have an incident energy $E_0$ (e.g., 6 MV), and fluence plane 240 along the beam axis outside the patient envelope at a known distance (e.g., 80 cm) from the isocenter.

At block 610 in FIG. 6, a target voxel ($i_0$, $j_0$, $k_0$) within target volume 146 is selected. This may be performed by selecting target voxel ($i_0$, $j_0$, $k_0$) with T($i_0$, $j_0$, $k_0$)>0 (i.e., non-zero probability of being a tumor). For example, the NCPDF associated with PDF T(i, j, k) may be sampled to locate a random target voxel within target volume 146. The NCPDF may be expressed as a bar graph with each bar denoting a bin with an upper (b+1) and lower bound (b), with each bin corresponding to a voxel (i, j, k). A random number between 0 and 1 is generated and the bin for which b≤ξ<b+1 is identified, thus selecting a random target voxel within target volume 146. It may also be more expedient to cycle sequentially (e.g., raster) through all non-zero dose deficit target voxels (i.e., TDDM(i, j, k)>0), but normalizing the weight of their call to the value of T(i, j, k).

At block 620 in FIG. 6, backprojection is performed from the target voxel ($i_0$, $j_0$, $k_0$) to radiation source 210 to determine a backprojection point (e.g., first fluence point K=(x, y) 242 in FIG. 4A and second fluence point 244 FIG. 4B) on fluence plane 240. Any suitable backprojection approach may be used. In one example, a simple backprojection operation may be used to determine a projection from the target voxel ($i_0$, $j_0$, $k_0$) to radiation source 210. In another example, a full adjoint Monte Carlo simulation to transport a particle from the target voxel ($i_0$, $j_0$, $k_0$) backwards to fluence plane 240, starting with zero energy and gaining in energy with each interaction as it advances towards fluence plane 240, where it should have an incident energy $E_0$ (e.g., 6 MV). This way, a single backprojection point may be projected onto fluence plane 240 at various angles 230 of interest, such as first point 242 at angle="a" and second point 244 at angle="b".

At block 630 in FIG. 6, multiple sets of particle histories may be initiated. For example, first set 410 of particle histories (e.g., h1 and h2) may be initiated from first backprojection point 242 on fluence plane 240 at angle="a" to multiple voxels 142 of treatment volume 142. Similarly, second set 420 of particle histories (e.g., h3 and h4) may be initiated from second backprojection point 242 on fluence plane 240 at angle="b" to multiple voxels 142 of treatment volume 142. Since particle histories 410/420 are initiated from point 242/244 that is backprojected from the target voxel ($i_0$, $j_0$, $k_0$) within target volume 146, particle histories 410/420 are expected to hit at least part of target volume 146 or the target voxel ($i_0$, $j_0$, $k_0$). In other words, target volume 146 may be thought as "calling" for particles until it has been sufficiently hit (e.g., desired dose $D_{TAR}$ and any other constraint(s) satisfied). This generally improves the efficiency of the particle transport simulation, with lower computational waste. This should be contrasted with conventional approach that starts at the source and requires calculation across the field, which results in some particles that never hit the target. This wastes time and effort because those particles will be assigned a low weight and has no benefit to the target.

First set 410 and second set 420 may each include any suitable number, N, of particle histories. Its size of the set may be determined using any suitable approach, such as by randomly sampling number N for each iteration of particle transport simulation. The appropriate size N may be chosen to get a meaningful "best answer" from a given fluence plane 240, such as to hit a particular target voxel 50-100 times. If N is too large, the calculation may become inefficient (since many histories may be discarded) and the answers obtained "lumpy" because the overall PDM is only updated at the end of each round. However, if N is too small, there may not be enough particle histories to select from.

The odds of hitting the target voxel ($i_0$, $j_0$, $k_0$) within target volume 146 may vary, but generally decreases with source-to-target distance (total path), changes in density or material, lower incident energy, etc. In some implementations, it is envisaged that hundreds of particle histories in set 410/420 may be required. N may also depend on the similarity of the particle histories in each round. For example, if there is no significant differentiation between the particle histories after a while (e.g., looking at variances in scattering angle and energy deposition), additional particle histories may not be required. Alternatively, variances may be induced using forced interactions with weighting that is consistent with the probability of occurrence.

During particle transport simulation, each particle history is randomly assigned with properties (e.g., fluence parameters) given their backprojection point 242/244, K=(x, y), on fluence plane 240, direction, energy (e.g., based on a predetermined source energy or selected from a set of possible starting energies). In practice, it may be desirable to extend the exact K=(x, y) birth point by a certain width (e.g., related electron transport kernel) to increase the chance of hitting the target voxel ($i_0$, $j_0$, $k_0$) that "called" for set of particle histories 410/420. This has the effect of "blurring" the source slightly for various particle histories in set 410/420.

Particle histories in set 410/420 will each travel on a path through treatment volume 140, emanating from backprojection point, K=(x, y), 242/244 until the particle either exits or its energy is completely absorbed by treatment volume 140. A particle history may also be "killed" if its cost is getting too high (e.g., they missed the target voxel or have a high cost). Further, to improve or maximize the validity of subsequent selection of "winning" history from set 410/420, the same sequence of random numbers may be reused to determine the individual interactions of each particle history in each set 410. Since each particle history is statistically independent of one another, multiple particle histories in set 410/420 may be transported in parallel.

Selecting Particle Histories

With reference to blocks 640 to 680 in FIG. 6, the selection of first set 410 or second set 420 according to block 340 in FIG. 3 and FIG. 530 in FIG. 5 will now be explained.

At block 640 in FIG. 6, a voxel-level cost ($c_{ijk}$) is determined for each voxel on a path travelled a particular particle history in set 410/420. The path extends from backprojection point 242/244, K=(x, y), on fluence plane 240 to voxels 142 treatment volume 140. Using the example in FIG. 4A and FIG. 4B, first set 410 may include particle histories h1 and h2, and second set 420 h3 and h4. Say if a particular particle history h2 travels along a path that includes example voxels v1=(1, 1, 1) and v2=(1, 1, 2), corresponding voxel-level costs $c_{v1}$ and $c_{v2}$ will be determined for respective voxels v1 and v2. This is then repeated for other particle histories in both first set 410 and second set 420.

Voxel-level cost ($c_{ijk}$) may be determined based on (i) a computed dose ($d_{ijk}$) deposited by the particle history (e.g., h2) on the voxel and (ii) a desired dose ($D_{ijk}$) for the voxel. As discussed above with reference to FIG. 4B, FIG. 5 and block 605 in FIG. 6, voxel-level cost ($c_{ijk}$) may be determined based on spatial information of the voxel (i, j, k). For example, one approach is to use $D_{ijk}=\min(D_{OAR}, \hat{d}_{min}(i,j,k))$ to represent a desired dose for a voxel (i, j, k) within OAR 148 or $D_{ijk}=\max(D_{TAR}, \hat{d}_{min}(i,j,k))$ for a voxel (i, j, k) within target volume 146. In this case, the voxel-level cost ($c_{ijk}$) may be determined as follows:

Spatially varying cost function: $c_{ijk}=(d_{ijk}-D_{ijk})^{2n+1}$.

In this case, rather than using the same $D_{TAR}$ 152 or $D_{OAR}$ 154 as the desired dose, the spatially varying voxel-level cost ($c_{ijk}$) is independent of all other voxels 142 within treatment volume 140. Such an approach preserves the spatial characteristics of the problem, allowing each voxel 142 in the patient to have a unique cost function that is derived from, for example, a dose, volume and position simultaneously.

Figure 7B:
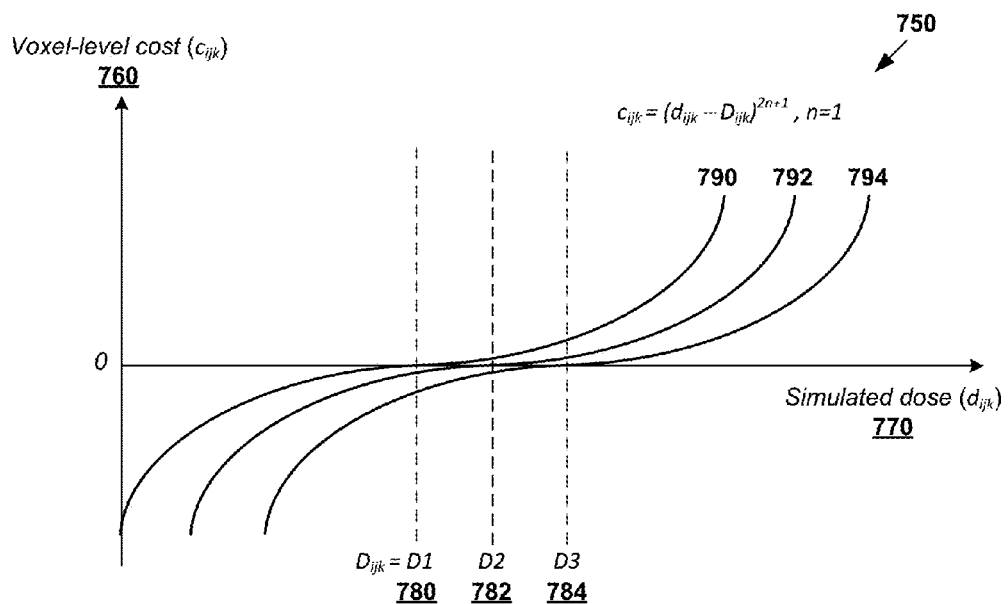
FIG. 7B is a simplified graph of voxel-level cost plotted as a function of simulated dose for a given desired dose.

To better illustrate the cost function, FIG. 7B is a simplified graph of voxel-level cost ($c_{ijk}$) plotted as a function of simulated dose ($d_{ijk}$) for a given desired dose ($D_{ijk}$). In this example, voxel-level cost ($c_{ijk}$) at 760 increases continuously from negative to zero as simulated dose ($d_{ijk}$) at 770 approaches the desired dose ($D_{ijk}$), and then grows steeply for as simulated dose ($d_{ijk}$) exceeds the desired dose ($D_{ijk}$). The slope of the cost function indicates how much "benefit" or "penalty" should be applied to a particular particle history if it is selected to deposit an incremental simulated dose ($d_{ijk}$) into target volume 146. Depending on the desired dose $D_{ijk}$ for a particular voxel (e.g., D1, D2 and D3), the resulting cost function may vary (see 780, 782, 784 and corresponding 790, 792 and 794). As such, the spatially varying cost function is able to capture the different requirements of different voxels 142 within treatment volume 140.

As discussed using the example in FIG. 7A, achievable dose $\hat{d}_{min}(i, j, k)$ may decrease as voxel 142 within target volume 146 is closer to surface 454 of target volume 146. For voxel 142 outside of target volume 146, achievable dose $\hat{d}_{min}(i, j, k)$ may also decrease as the voxel is further away from surface 454 of target volume 146. Further, although a constant integer n in the above example, the slope of the cost function ($c_{ijk}$) may depend on a particular voxel, i.e., replacing n with $n_{ijk}$ to further tailor cost $c_{ijk}$ to that voxel.

At block 650 in FIG. 6, a cumulative cost ($C_h$) is determined for each particle history in first set 410 and second set 420 based on the voxel-level cost ($c_{ijk}$) is determined for each voxel on a path travelled by the particle history. In one example, a negative voxel-level cost ($c_{ijk}$) may represent a benefit that adds an incremental dose ($d_{ijk}$) to a particular voxel. The individual (negative or positive) costs for each particle history are summed up until either particle exits the patient or deposits all of its energy within the patient.

For example, cumulative cost ($C_h$) may be determined as $C_h = \Sigma_{ijk} c_{ijk} d_{ijk}$ that is summed and evaluated over each (i, j, k) voxel over which a particle-shower deposits dose $d_{ijk}$ and incurs the voxel-level cost ($c_{ijk}$). Here, $c_{ijk} d_{ijk}$ represents a voxel's contribution to the cumulative cost ($C_h$), i.e., simulated dose ($d_{ijk}$) deposited by the particle history weighted by voxel-level cost ($c_{ijk}$) and the resulting $C_h$ representing a weighted sum of the voxel-level costs. Using the above example, for particle history h2 that incurs costs $c_{v1}$ and $c_{v2}$ at voxels v1 and v2 respectively, its cumulative cost may be determined as $C_{h2} = c_{v1} d_{v1} + c_{v2} d_{v2}$. Block 650 is then repeated for other particle histories, such as h1 in first set 410 and h3 and h4 in second set 420, to determine corresponding cumulative costs, i.e., $C_{h1}$, $C_{h3}$ and $C_{h4}$.

Using the spatially varying cost function, voxel-level cost ($c_{ijk}$) and therefore cumulative cost ($C_h$) have an embedded dependency on distance 452 from each voxel 142 to surface 454 of target volume 146 along the direction of radiation beam 220. See also FIG. 4B and FIG. 7A. In this case, spatial information 450 about dose distributions may therefore be incorporated into the cost function by replacing $D_{TAR}$ in the PTV dose cost function or $D_{OAR}$ in the OAR dose cost function with a dose that is modulated by the expected dose given the location of the target voxel.

At block 660 in FIG. 6, first set 410 or second set 420 (see FIG. 4A and FIG. 4B) may be selected based on cumulative costs ($C_h$) associated with respective particle histories. In particular, once all particle histories in first set 410 and second set 420 have finished transporting (e.g., electron-photon transport history is complete), they may be ranked from according to their respective cumulative costs ($C_h$), such as from the most favorable (i.e., lowest cost) to the least favorable (i.e., highest cost).

The cumulative cost ($C_h$) may be interpreted as a "score" representing the positive or negative benefit of the particle history. Any selection criteria may be used to select particle histories having the most favorable cumulative cost, such as by selecting a certain percentage (e.g., 10%) or number of particle histories. Using the example in FIG. 4A and FIG. 4B, first set 410 may be ranked according to $C_{h1}$ and $C_{h2}$ (i.e., first cumulative costs) and second set 420 according to $C_{h3}$ and $C_{h4}$ (i.e., second cumulative costs). For example, first set 410 may be selected over second set 420 if a sum of the first cumulative costs (e.g., sum of $C_{h1}$ and $C_{h2}$) is greater than a sum of the second cumulative costs (e.g., sum of $C_{h3}$ and $C_{h4}$). Although first set 410 and second set 420 are discussed here, any number of sets may be used in practice. For example, if five sets are initiated for respective angles "a", "b", "c", "d" and "e" in FIG. 2, the different sets may be similarly ranked and selected according to cumulative costs associated with respective particle histories in each set.

In addition to the local, voxel-level cost functions, any global dose-volume histogram (DVH) objectives may be used to govern the bulk properties of target volume 146 and OAR 148. Moreover, hard constraints may be built into the selection of particle histories. For example, the hard constraints may be designed to reject a particle that comes from a particular direction or crosses a volume, for example to block out areas around artificial (metal) joint implants or directions that would cause a collision or some other problem. There might also be hard dose constraints. If there is an adjoining radiation filed, the maximum dose should not be exceeded. For example, spine dose can never exceed 45 Gray. A particle will be rejected if it deposits dose into a spine voxel that has already reach the maximum of 45 Gray. Should it be a winning history, it will be ignored and another set of particle histories called. If a particle history does not satisfy a predetermined constraint, it may be determined to be out of contention and assigned a large positive cost (e.g., maximum value) such that it will not be selected.

At block 670 in FIG. 6, various simulation data may be updated. For example, after the selection process at block 660, the dose deposited by particle histories in selected first set 410 or second set 420 may be added to the PDM. For example, for particle history h2, the incremental dose deposited at voxels v1=(1, 1, 1) and v2=(1, 1, 2) may be added to respective matrix elements in the PDM to reflect the new accumulated dose values.

The TDDM may be updated accordingly to deduct the incremental dose ($d_{ijk}$) from corresponding matrix elements. The PCM may also be updated with the voxel-level cost ($c_{ijk}$). Corresponding fluence parameters required to initiate a first set 410 or second set 420, which contribute to the final fluence map 250, will be stored. For example, intensity profile at backprojection point K=(x, y) 242/244 may be stored along with the direction and energy of the particle. A 2D map may be stored for photons, and a 3D layered map for protons. All other particle histories (e.g., h1 and h4) will be discarded. Any bulk dose-volume statistics may be updated, and corresponding bulk dose-volume objectives recomputed (if in use). For example, the statistics may include dose volume histogram objective, mean dose, median dose, max dose, min dose, etc. For example, a common set of goals for lung tissue is: V5<60%; V10<40%; V20<30%. This means, of the total lung volume, less than 5% of the volume (voxels) should be at 60% of the prescribed dose, etc.

At block 680 in FIG. 6, it is determined whether one or more stopping conditions are satisfied. If not satisfied, blocks 610 to 680 are repeated, but otherwise, process 600 proceeds to block 690. Any suitable stopping condition(s)

may be used. Termination may occur when dose deficit, TDDM(i, j, k), is zero for all voxels, or it is not possible to add further incremental dose to the target voxel without violating some other objectives (e.g., OAR dose goal). For example, unless a tumor has reached its prescription, it will request for more particle histories from the beam angles 230 of interest.

Once the stopping condition(s) are met, traditional optimization methods may also be used to balance the advantage of adding more dose to the target voxel ($i_0$, $j_0$, $k_0$) in target volume 146 against the disadvantage of adding more dose to OAR 148. It is believed that by careful selection of the global objective function, the simulation may generally be terminated when additional particle histories fail to improve to overall cost function. Normal termination criteria may apply, such as terminating the simulation if over a set of N particle histories, the overall cost function does not increase by more than x %, etc.

Alternatively, each round of particle histories may end by allowing each winning history to be weighted, such as to add exactly the amount of the remaining dose deficit in the target for each voxel it touches. For example, if there were multiple winners, the dose deficient could be split equally between them. If this causes hard constraints to be violated, the weight of the history is de-escalated until it is satisfies all hard constraints. In the early rounds, the distributions may improve quickly with these additions, but at some point the distribution either does not improve significantly, or gets worse, which causes the end of the simulation.

Determining Treatment Plan

At block 690 in FIG. 6, treatment plan 170 may be determined based on fluence parameters resulting from all "winning" particle histories selected at block 660. The fluence parameters may represent the optimal set of beam fluences, having been directly identified as the particle histories having the best cost functions during the particle transport simulation. Although first set 410 and second set 420 are used as examples throughout the present disclosure, it will be appreciated that additional or alternative sets may be used to determine treatment plan 170.

Figure 8:
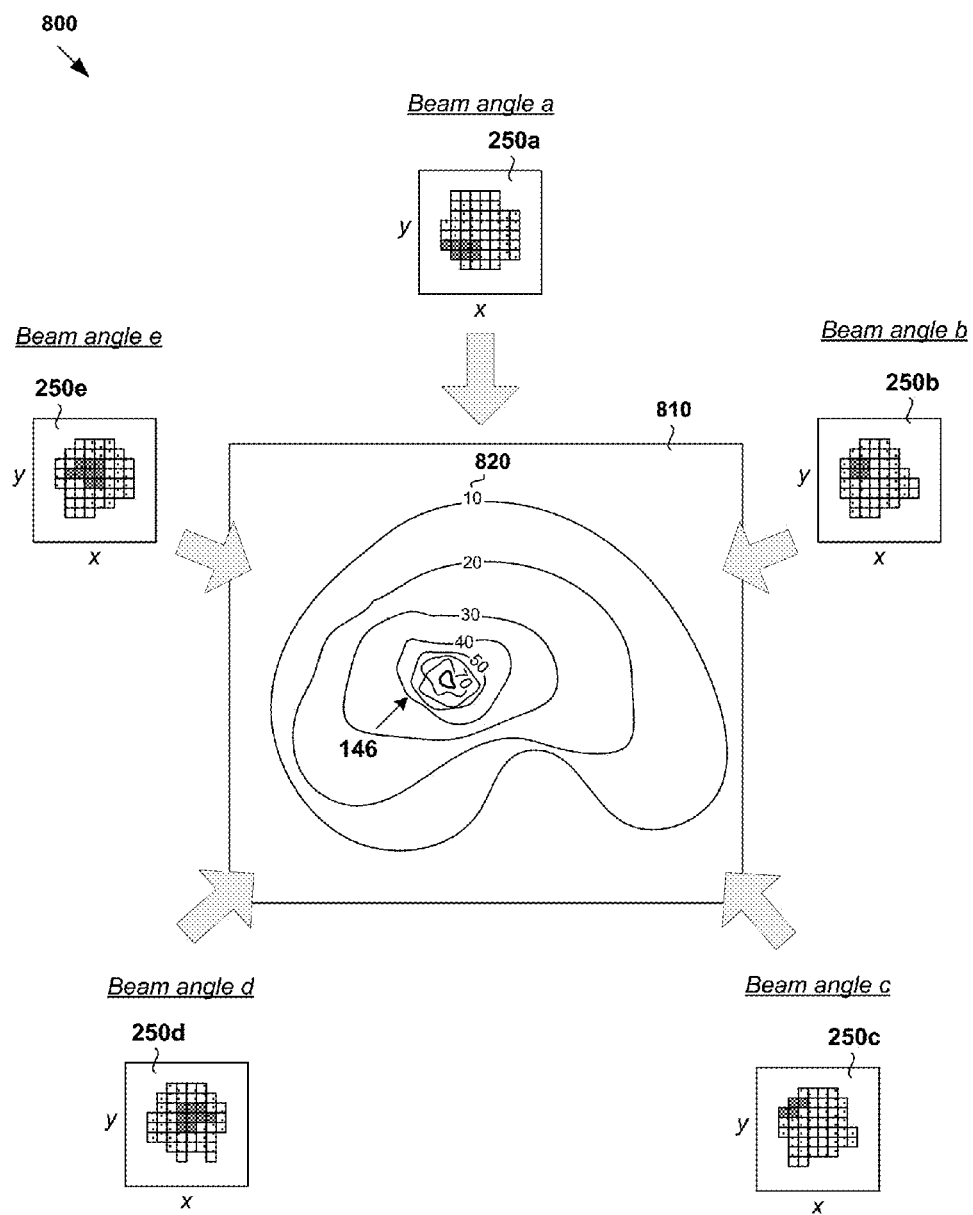
FIG. 8 is a schematic diagram of an example treatment plan determined using the example process in FIG. 6.

In one example, the fluence parameters may be in the form of fluence maps 250 discussed using FIG. 2. FIG. 8 is a schematic diagram of example treatment plan 170 determined using example process 600 in FIG. 6. In this example, composite map 810 represents various radiation doses that can be delivered to the patient based on fluence maps 250a, 250b, 250c, 250d and 250e of corresponding beam angles 230 "a", "b", "c", "d" and "e". Each contour on composite map 810 represents a particular value 820 of radiation dose, such as 10 Gray, 20 Gray, and so on. As can be seen, a more targeted treatment may be delivered, with higher radiation doses at target volume 146 and lower radiation doses at outside of target volume 146.

Once treatment plan 170 is determined, a radiotherapy treatment system may then deliver radiotherapy treatment to the patient. For example, a beam shaping device (e.g., multileaf collimator (MLC)) may be attached to radiation source 210 to shape or form radiation beam 220 according to corresponding fluence maps 250a, 250b, 250c, 250d and 250e. Radiation dose is deposited into tissue lying along the path of each radiation beam 220, and as such, a much greater amount of energy is deposited in the region where all radiation beams 220 from different angles 230 overlap.

In the case of MLC, fluence maps 250a, 250b, 250c, 250d and 250e may be converted into leaf sequences using a Leaf Motion Calculator (LMC). Each leaf of the MLC is adjustable to act as a filter to block or allow radiation through. Also, the longer an MLC leaf is open at certain point (x, y), the higher the radiation dose that is delivered from that position.

Example Systems

Figure 9:
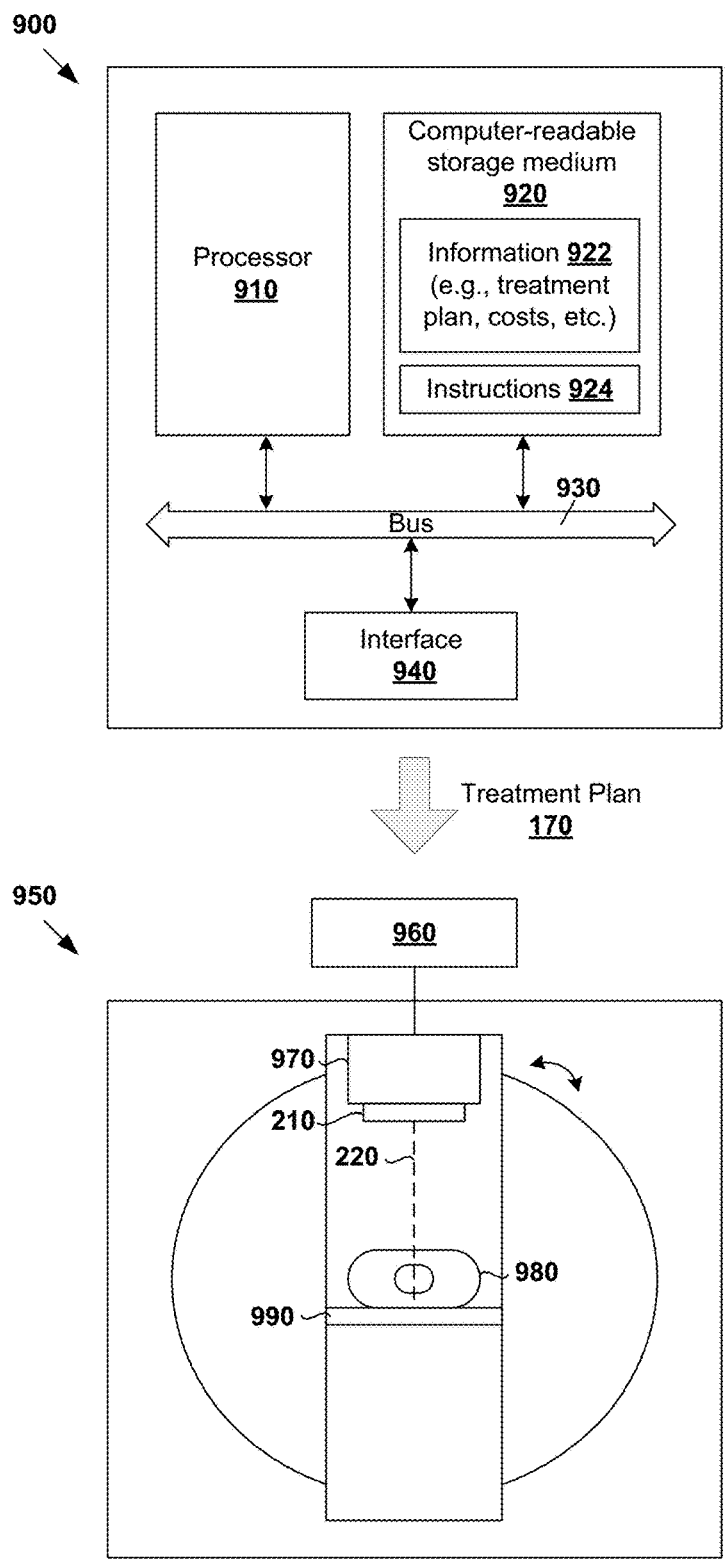
FIG. 9 is a schematic diagram of a system that includes an example computer system for radiotherapy treatment planning and an example radiotherapy treatment system for treatment delivery.

The above examples can be implemented by hardware, software or firmware or a combination thereof. FIG. 9 is a schematic diagram of a system that includes example computer system 900 for radiotherapy treatment planning 160 and example radiotherapy treatment system 950 for treatment delivery 180.

Example computer system 905 (also known as a treatment planning system) may include processor 910, computer-readable storage medium 920, interface 940 to interface with radiotherapy treatment system 950, and bus 930 that facilitates communication among these illustrated components and other components. Processor 910 is to perform processes described herein with reference to FIG. 1 to FIG. 8. Computer-readable storage medium 920 may store any suitable information 922, such as information relating to treatment plan 170, cumulative costs, voxel-level costs, particle histories, etc. Computer-readable storage medium 920 may further store computer-readable instructions 924 which, in response to execution by processor 910, cause processor 910 to perform processes described herein with reference to FIG. 1 to FIG. 8.

As explained with reference to FIG. 2, example radiotherapy treatment system 950 may include rotatable gantry 970 to which radiation source 210 is attached. During treatment delivery 180, gantry 970 is rotated around patient 980 supported on structure 990 to emit radiation beam 220 at various beam angles 230, as explained with reference to FIG. 2. Radiotherapy treatment system 950 may further include controller 960 to obtain (e.g., receive, retrieve from storage) treatment plan 170 devised by example treatment planning system 900 to control gantry 970, radiation source 210 and radiation beam 220 to deliver radiotherapy treatment.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof.

Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

We claim:

1. A method of determining a treatment plan for a radiotherapy treatment system to deliver radiotherapy treatment to a patient, the method comprising:

performing a particle transport simulation to initiate a first set of particle histories and a second set of particle histories from a radiation source of the radiotherapy treatment system to a treatment volume with multiple voxels representing an anatomy of the patient, wherein the first set is associated with a first radiation beam angle of the radiation source and the second set is associated with a second radiation beam angle of the radiation source and wherein performing the particle transport simulation further comprises:

selecting a target voxel within a target volume of the treatment volume;

backprojecting from the target voxel to the radiation source to determine a first backprojection point on a first fluence plane associated with the first radiation beam angle of the radiation source;

backprojecting from the target voxel to the radiation source to determine a second backprojection point on a second fluence plane associated with the second radiation beam angle of the radiation source; and initiating the first particle history from the first backprojection point and the second particle history from the second backprojection point to the treatment volume;

determining first cumulative costs associated with respective particle histories in the first set and second cumulative costs associated with respective particle histories in the second set, wherein each of the first cumulative costs and second cumulative costs is determined based on voxel-level costs associated with respective voxels on a path travelled by the associated particle history and wherein, for each particle history in the first set and the second set, each of the voxel-level costs associated with respective voxels is determined based on (i) a computed dose deposited by the particle history on the associated voxel and (ii) a determined dose for the associated voxel;

selecting the first set or second set based on the first cumulative costs and second cumulative costs; and determining the treatment plan based on the selected first set or second set.

2. The method of claim 1, wherein the determined dose is a spatially-varying determined dose that is determined based on spatial information of the associated voxel.

3. The method of claim 1, wherein selecting the first set or second set comprises:

ranking the first set based on the first cumulative costs and the second set based on the second cumulative costs; and selecting the first set or the second set based on the ranking.

4. The method of claim 1, wherein selecting the target voxel within the target volume of the treatment volume comprises:

determining a probability of the target voxel being within the target volume based on a probability distribution function; and selecting the target voxel based on the probability.

5. The method of claim 4, wherein determining the probability of the target voxel being within the target volume comprises:

determining the probability distribution function to account for an uncertainty associated with the target volume due to a motion of the patient when image data of the patient is captured during image acquisition.

6. The method of claim 1, wherein the particle transport simulation is a Monte Carlo simulation, and any of the particle histories is assigned with fluence parameters including fluence maps representing intensity profiles of a radiation beam of the radiation source.

7. A non-transitory computer-readable storage medium that includes a set of instructions which, in response to execution by a processor of a computer system, cause the processor to perform a method of determining a treatment plan for a radiotherapy treatment system to deliver radiotherapy treatment to a patient, the method comprising:

performing a particle transport simulation to initiate a first set of particle histories and a second set of particle histories from a radiation source of the radiotherapy treatment system to a treatment volume with multiple voxels representing an anatomy of the patient, wherein the first set is associated with a first radiation beam angle of the radiation source and the second set is associated with a second radiation beam angle of the radiation source and wherein performing the particle transport simulation further comprises:

selecting a target voxel within a target volume of the treatment volume;

backprojecting from the target voxel to the radiation source to determine a first backprojection point on a first fluence plane associated with the first radiation beam angle of the radiation source;

backprojecting from the target voxel to the radiation source to determine a second backprojection point on a second fluence plane associated with the second radiation beam angle of the radiation source; and initiating the first particle history from the first backprojection point and the second particle history from the second backprojection point to the treatment volume;

determining first cumulative costs associated with respective particle histories in the first set and second cumulative costs associated with respective particle histories in the second set, wherein each of the first cumulative costs and second cumulative costs is determined based on voxel-level costs associated with respective voxels on a path travelled by the associated particle history and wherein, for each particle history in the first set and the second set, each of the voxel-level costs associated with respective voxels is determined based on (i) a computed dose deposited by the particle history on the associated voxel and (ii) a determined dose for the associated voxel;

selecting the first set or second set based on the first cumulative costs and second cumulative costs; and determining the treatment plan based on the selected first set or second set.

8. A computer system configured to determine a treatment plan for a radiotherapy treatment system to deliver radiotherapy treatment to a patient, the computer system comprising: a processor and a non-transitory computer-readable medium having stored thereon instructions that, when executed by the processor, cause the processor to:

perform a particle transport simulation to initiate a first set of particle histories and a second set of particle histories from a radiation source of the radiotherapy treatment system to a treatment volume with multiple voxels representing an anatomy of the patient, wherein the first set is associated with a first radiation beam angle of the radiation source and the second set is associated with a second radiation beam angle of the radiation source and wherein the performing the particle transport simulation further comprises:

selecting a target voxel within a target volume of the treatment volume;

backprojecting from the target voxel to the radiation source to determine a first backprojection point on a first fluence plane associated with the first radiation beam angle of the radiation source;
backprojecting from the target voxel to the radiation source to determine a second backprojection point on a second fluence plane associated with the second radiation beam angle of the radiation source; and
initiating the first particle history from the first backprojection point and the second particle history from the second backprojection point to the treatment volume;
determine first cumulative costs associated with respective particle histories in the first set and second cumulative costs associated with respective particle histories in the second set, wherein each of the first cumulative costs and second cumulative costs is determined based on voxel-level costs associated with respective voxels on a path travelled by the associated particle history and wherein, for each particle history in the first set and the second set, each of the voxel-level costs associated with respective voxels is determined based on (i) a computed dose deposited by the particle history on the associated voxel and (ii) a determined dose for the associated voxel;
select the first set or second set based on the first cumulative costs and second cumulative costs; and
determine the treatment plan based on the selected first set or second set.

9. A method of determining a treatment plan for a radiotherapy treatment system to deliver radiotherapy treatment to a patient, the method comprising:
performing a particle transport simulation to initiate a first set of particle histories and a second set of particle histories from a radiation source of the radiotherapy treatment system to a treatment volume with multiple voxels representing an anatomy of the patient, wherein the first set is associated with a first radiation beam angle of the radiation source and the second set is associated with a second radiation beam angle of the radiation source and wherein performing the particle transport simulation further comprises:
selecting a target voxel within a target volume of the treatment volume;
backprojecting from the target voxel to the radiation source to determine a first backprojection point on a first fluence plane associated with the first radiation beam angle of the radiation source;
backprojecting from the target voxel to the radiation source to determine a second backprojection point on a second fluence plane associated with the second radiation beam angle of the radiation source; and
initiating the first particle history from the first backprojection point and the second particle history from the second backprojection point to the treatment volume;
determining, for each particle history the first set and the second set, voxel-level costs associated with respective voxels on a path travelled by the particle history, wherein each voxel-level cost is determined based on (i) a computed dose deposited by the particle history on the associated voxel and (ii) a spatially-varying determined dose of the associated voxel;
selecting the first set or the second set based on the voxel-level costs; and
determining the treatment plan based on the selected first set or second set.

10. The method of claim 9, wherein determining voxel-level costs associated with respective voxels comprises:
determining, for each of the voxels, the spatially-varying determined dose based on spatial information of the voxel.

11. The method of claim 10, wherein the spatial information comprises one or more of the following: a distance of the voxel from a surface of a target volume within treatment volume, a spatially-varying probability density function associated with the voxel being located in a target volume or organ-at-risk and function of a region in which the voxel is located.

12. The method of claim 9, wherein:
the method further comprises: based on the voxel-level costs, determining first cumulative costs associated with respective particle histories in the first set and second cumulative costs associated with respective particle histories in the second set; and
selecting the first set or the second set is based on the first cumulative costs and second cumulative costs.

13. The method of claim 9, wherein selecting the target voxel within the target volume of the treatment volume comprises:
determining a probability of the target voxel being within the target volume based on a probability distribution function; and
selecting the target voxel based on the probability.

14. The method of claim 13, wherein determining the probability of the target voxel being within the target volume comprises:
determining the probability distribution function to account for an uncertainty associated with the target volume due to a motion of the patient when image data of the patient is captured during image acquisition.

15. The method of claim 9, wherein the particle transport simulation is a Monte Carlo simulation, and any of the particle histories is assigned with fluence parameters including fluence maps representing intensity profiles of a radiation beam of the radiation source.

16. A non-transitory computer-readable storage medium that includes a set of instructions which, in response to execution by a processor of a computer system, cause the processor to perform a method of determining a treatment plan for a radiotherapy treatment system to deliver radiotherapy treatment to a patient, the method comprising:
performing a particle transport simulation to initiate a first set of particle histories and a second set of particle histories from a radiation source of the radiotherapy treatment system to a treatment volume with multiple voxels representing an anatomy of the patient, wherein the first set is associated with a first radiation beam angle of the radiation source and the second set is associated with a second radiation beam angle of the radiation source and wherein performing the particle transport simulation further comprises:
selecting a target voxel within a target volume of the treatment volume;
backprojecting from the target voxel to the radiation source to determine a first backprojection point on a first fluence plane associated with the first radiation beam angle of the radiation source;
backprojecting from the target voxel to the radiation source to determine a second backprojection point on a second fluence plane associated with the second radiation beam angle of the radiation source; and
initiating the first particle history from the first backprojection point and the second particle history from the second backprojection point to the treatment volume;

determining, for each particle history the first set and the second set, voxel-level costs associated with respective voxels on a path travelled by the particle history, wherein each voxel-level cost is determined based on (i) a computed dose deposited by the particle history on the associated voxel and (ii) a spatially-varying determined dose of the associated voxel;

selecting the first set or the second set based on the voxel-level costs; and determining the treatment plan based on the selected first set or second set.

17. A computer system configured to determine a treatment plan for a radiotherapy treatment system to deliver radiotherapy treatment to a patient, the computer system comprising: a processor and a non-transitory computer-readable medium having stored thereon instructions that, when executed by the processor, cause the processor to:

perform a particle transport simulation to initiate a first set of particle histories and a second set of particle histories from a radiation source of the radiotherapy treatment system to a treatment volume with multiple voxels representing an anatomy of the patient, wherein the first set is associated with a first radiation beam angle of the radiation source and the second set is associated with a second radiation beam angle of the radiation source and wherein performing the particle transport simulation further comprises:

selecting a target voxel within a target volume of the treatment volume;

backprojecting from the target voxel to the radiation source to determine a first backprojection point on a first fluence plane associated with the first radiation beam angle of the radiation source;

backprojecting from the target voxel to the radiation source to determine a second backprojection point on a second fluence plane associated with the second radiation beam angle of the radiation source; and initiating the first particle history from the first backprojection point and the second particle history from the second backprojection point to the treatment volume;

determine, for each particle history the first set and the second set, voxel-level costs associated with respective voxels on a path travelled by the particle history, wherein each voxel-level cost is determined based on (i) a computed dose deposited by the particle history on the associated voxel and (ii) a spatially-varying determined dose of the associated voxel;

select the first set or the second set based on the voxel-level costs; and determine the treatment plan based on the selected first set or second set.

* * * * *